(12) United States Patent
Natesan

(10) Patent No.: US 11,992,647 B2
(45) Date of Patent: May 28, 2024

(54) VALVE RETAINER RING AND RELATED SYSTEMS AND METHODS

(71) Applicant: Becton, Dickinson and Company, Franklin Lakes, NJ (US)

(72) Inventor: Mohankumar Natesan, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 114 days.

(21) Appl. No.: 17/565,189

(22) Filed: Dec. 29, 2021

(65) Prior Publication Data

US 2022/0226631 A1 Jul. 21, 2022

Related U.S. Application Data

(60) Provisional application No. 63/139,640, filed on Jan. 20, 2021.

(51) Int. Cl.
*A61M 39/22* (2006.01)
*A61M 5/14* (2006.01)
*A61M 5/158* (2006.01)
*A61M 25/06* (2006.01)
*A61M 39/10* (2006.01)

(52) U.S. Cl.
CPC .......... *A61M 39/225* (2013.01); *A61M 5/158* (2013.01); *A61M 25/0606* (2013.01);
(Continued)

(58) Field of Classification Search
CPC ................ A61M 39/225; A61M 5/158; A61M 25/0606; A61M 39/10; A61M 2005/1403; A61M 2039/1077; A61M 2039/242; A61M 2039/0633; A61M 2039/2433; A61M 39/20; A61M 39/06; A61M 2039/0205; A61M 25/0097; A61M 39/1011; A61M 39/105; A61M 39/22; A61M 2005/1587

See application file for complete search history.

(56) References Cited

U.S. PATENT DOCUMENTS 4,038,983 A * 8/1977 Mittleman ............ A61M 39/24
604/185
5,098,405 A 3/1992 Peterson
(Continued)

FOREIGN PATENT DOCUMENTS

AU 2012318631 4/2014
AU 2014274933 A1 1/2016
(Continued)

*Primary Examiner* — Theodore J Stigell
(74) *Attorney, Agent, or Firm* — Kirton McConkie; Whitney Blair; Kevin Stinger

(57) ABSTRACT

A catheter system may include a catheter assembly. The catheter assembly may include the catheter adapter, which may include a distal end, a proximal end, an inner surface forming a lumen, the lumen extending through the distal end and the proximal end, and a side port disposed between the distal end and the proximal end. The catheter assembly may include an annular valve, which may be disposed within the lumen and aligned with the side port. The annular valve may seal a fluid pathway from the side port to the lumen. The catheter assembly may include a retainer ring disposed proximal and/or proximate the annular valve within the lumen. The catheter assembly may include a catheter extending distally from the distal end of the catheter adapter.

20 Claims, 3 Drawing Sheets

(52) U.S. Cl.
CPC ..... *A61M 39/10* (2013.01); *A61M 2005/1403* (2013.01); *A61M 2039/1077* (2013.01)

(56) References Cited

U.S. PATENT DOCUMENTS

| | | | | |
|---|---|---|---|---|
| 6,638,250 B2* | 10/2003 | Wechler | ................ | A61M 39/24 604/257 |
| 8,622,972 B2* | 1/2014 | Nystrom | ................ | A61M 25/06 604/167.03 |
| 2014/0364809 A1 | 12/2014 | Isaacson et al. | | |
| 2017/0348518 A1* | 12/2017 | Ma | .................... | A61M 25/0097 |
| 2020/0094026 A1 | 3/2020 | Isaacson et al. | | |

FOREIGN PATENT DOCUMENTS

| | | | |
|---|---|---|---|
| AU | 2019203957 A1 | 6/2019 | |
| AU | 2020244445 A1 | 10/2020 | |
| BR | 112015030658 A2 | 7/2017 | |
| CA | 2914701 A1 | 12/2014 | |
| CN | 105705191 A | 6/2016 | |
| CN | 111991673 A | 11/2020 | |
| DE | 202007006190 | * | 9/2007 |
| EP | 1197242 | 4/2002 | |
| EP | 3003450 | 4/2016 | |
| EP | 3622999 A1 | 3/2020 | |
| EP | 3928822 A1 | 12/2021 | |
| ES | 2780697 T3 | 8/2020 | |
| ES | 2891005 T3 | 1/2022 | |
| JP | 2016523136 A | 8/2016 | |
| JP | 2019055264 A | 4/2019 | |
| JP | 2021058671 A | 4/2021 | |
| JP | 6877400 B2 | 5/2021 | |
| WO | 2008052791 A1 | 5/2008 | |
| WO | 2014197656 A1 | 12/2014 | |
| WO | 2018217781 | 11/2018 | |
| WO | 2020242878 | 12/2020 | |

* cited by examiner

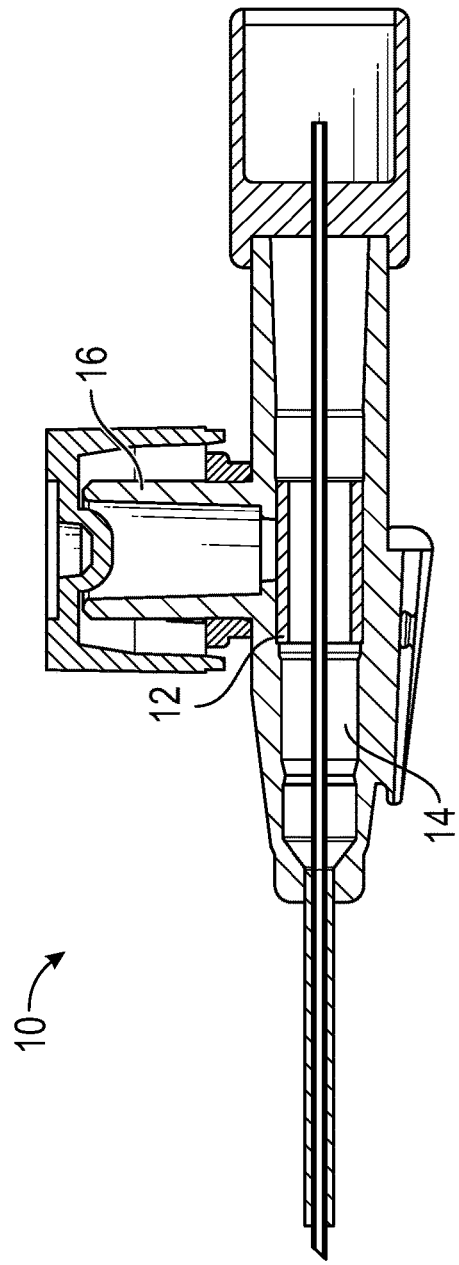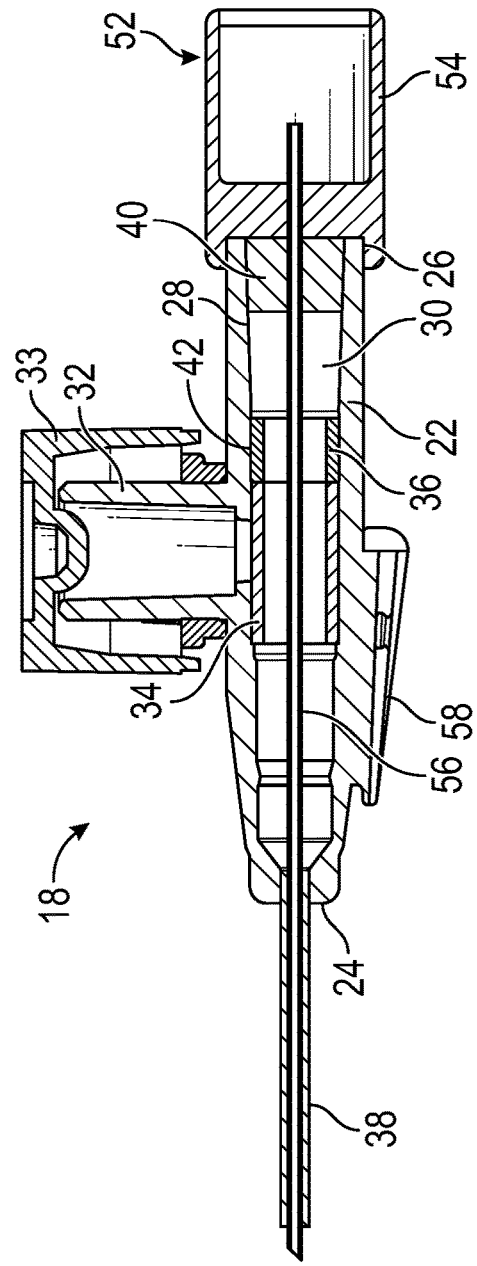

VALVE RETAINER RING AND RELATED SYSTEMS AND METHODS

RELATED APPLICATIONS

This application claims benefit of U.S. Provisional Patent Application No. 63/139,640, filed on Jan. 20, 2021, entitled VALVE RETAINER RING AND RELATED SYSTEMS AND METHODS, which is incorporated herein in its entirety.

BACKGROUND

Catheters are commonly used for a variety of infusion therapies. Catheters may be used for infusing normal saline solution, various medicaments, total parenteral nutrition, or other fluids into a patient. Catheters may also be used to withdraw blood from the patient for diagnostic or other purposes.

A common type of catheter is a peripheral intravenous catheter ("PIVC") that is "over-the-needle." As its name implies, the PIVC that is over-the-needle may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow angle through the skin into the vasculature of the patient.

In order to verify proper placement of the introducer needle and/or the PIVC in the blood vessel, a clinician generally confirms that there is "flashback" of blood in a flashback chamber of the catheter assembly. Once placement of the needle has been confirmed, the clinician may remove the introducer needle, leaving the PIVC in place for future fluid infusion.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices, systems, and methods. In particular, the present disclosure relates to a retainer ring and related systems and methods to facilitate securement of a valve within a catheter adapter. In some embodiments, a catheter system may include the catheter assembly. In some embodiments, the catheter assembly may include the catheter adapter, which may include a distal end, a proximal end, an inner surface forming a lumen, the lumen extending through the distal end and the proximal end, and a side port disposed between the distal end and the proximal end.

In some embodiments, the catheter assembly may include an annular valve, which may be disposed within the lumen and aligned with the side port. In some embodiments, the annular valve may seal a fluid pathway from the side port to the lumen. In some embodiments, the catheter assembly may include a retainer ring disposed proximal and/or proximate the annular valve within the lumen. In some embodiments, the catheter assembly may include a catheter extending distally from the distal end of the catheter adapter.

In some embodiments, the inner surface of the catheter adapter may include an undercut. In some embodiments, the retainer ring may be disposed within the undercut. In some embodiments, the annular valve may include silicon. In some embodiments, the annular valve may be cylindrical. In some embodiments, the retainer ring may be formed by molding. In some embodiments, the retainer ring may be plastic.

In some embodiments, the catheter system may include a needle assembly. In some embodiments, the needle assembly may include a needle hub and an introducer needle extending distally from the needle hub and through the retainer ring, the annular valve, and the catheter. In some embodiments, the side port may extend from a top of the catheter adapter. In some embodiments, the side port may be configured to receive a syringe. In some embodiments, the retainer ring is configured to reduce proximal movement of the annular valve in response to fluid infusion through the side port that opens the annular valve.

In some embodiments, a method of flushing the catheter assembly may include coupling an infusion device to the side port of the catheter adapter of the catheter assembly. In some embodiments, the method may include activating the infusion device. In some embodiments, in response to activating the infusion device, the annular valve may be opened to allow fluid to flow from the side port into the lumen. In some embodiments, in response to activating the infusion device, a proximal end of the annular valve may be forced against the retainer ring and the retainer ring may remain in place. In some embodiments, the infusion device may include a syringe. In some embodiments, activating the infusion device may include depressing a plunger of the syringe. In some embodiments, the method may include uncoupling and removing the needle assembly from the catheter adapter. In some embodiments, the infusion device may be activated after the needle assembly is uncoupled and removed from the catheter adapter.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1 is a cross-sectional view of a prior art catheter system;

FIG. 2A is a cross-sectional view of a catheter system, illustrating an example retainer ring, according to some embodiments;

DESCRIPTION OF EMBODIMENTS

Referring now to FIG. 1, a prior art catheter system 10 is illustrated. The prior art catheter system includes an annular valve 12 disposed in a catheter adapter lumen 14. The annular valve 12 is often moved proximally in response to fluid infusion through a side port 16 of the prior art catheter system 10. Proximal movement of the annular valve 12 may prevent the annular valve 12 from sealing the side port 16, and thus may result in leakage from the catheter adapter lumen 14 through the side port 16 following fluid infusion.

Figure 2B:
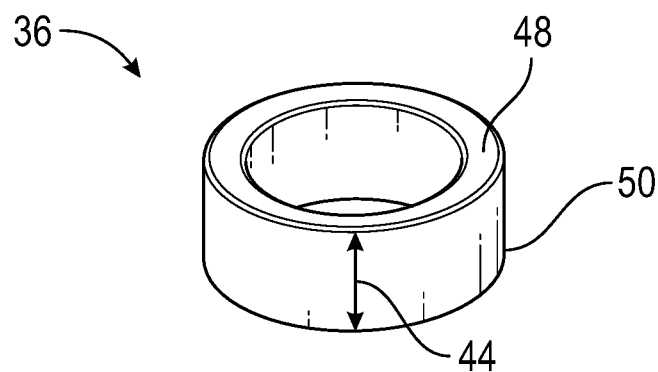
FIG. 2B is an upper perspective view of the retainer ring, according to some embodiments.
Figure 2C:
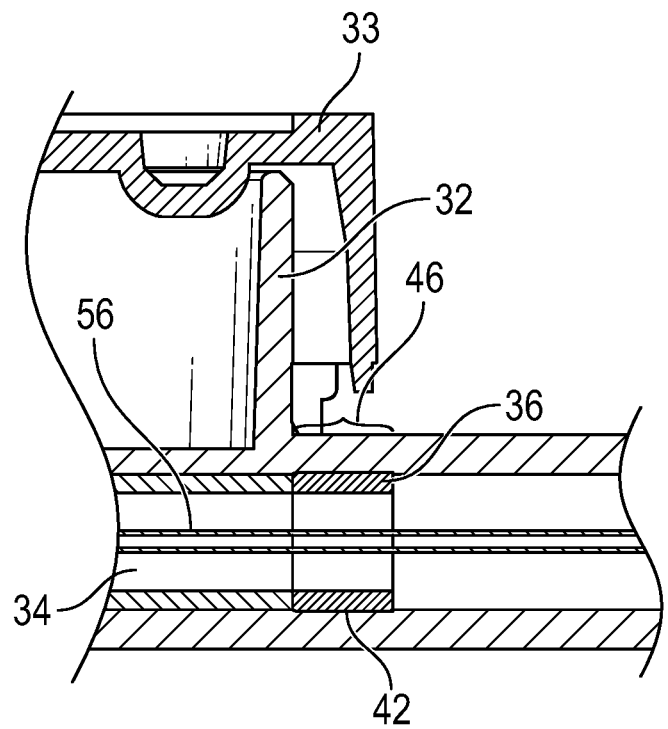
FIG. 2C is an enlarged cross-sectional view of a portion of the catheter system of FIG. 2A, according to some embodiments.

Referring now to FIGS. 2A-2C, a catheter system 18 is illustrated, according to some embodiments. In some embodiments, the catheter system 18 may include a catheter assembly 20. In some embodiments, the catheter assembly 20 may include a catheter adapter 22, which may include a distal end 24, a proximal end 26, an inner surface 28 forming a lumen 30. In some embodiments, the catheter assembly 20 may include the lumen 30 extending through the distal end 24 and the proximal end 26. In some embodiments, the catheter assembly 20 may include a side port 32 disposed between the distal end 24 and the proximal end 26. In some embodiments, the catheter assembly 20 may include a cap 33 removably coupled to the side port 32.

In some embodiments, the catheter assembly 20 may include an annular valve 34, which may be disposed within the lumen 30 and aligned with the side port 32. In some embodiments, the annular valve 34 may seal a fluid pathway from the side port 32 to the lumen 30. In some embodiments, the annular valve 34 may include silicon or another suitable material that allows an edge of the annular valve 34 to depress and open the fluid pathway from the side port 32 to the lumen 30 in response to fluid infusion through the side port 32. In some embodiments, the annular valve 34 may be cylindrical.

In some embodiments, the catheter assembly 20 may include a retainer ring 36 disposed proximal and/or proximate the annular valve 34 within the lumen 30. In some embodiments, the retainer ring 36 may be contacting the annular valve 34. In some embodiments, the catheter assembly 20 may include a catheter 38 extending distally from the distal end 24 of the catheter adapter 22. In some embodiments, the catheter 38 may include a peripheral intravenous catheter (PIVC), a midline catheter, a peripherally-inserted central catheter, or another suitable type of catheter.

In some embodiments, the catheter assembly 20 may include a septum 40, which may be disposed proximal to the retainer ring 36 and the annular valve 34. In some embodiments, the septum 40 may include silicon or another suitable material.

In some embodiments, the inner surface 28 of the catheter adapter 22 may include an undercut 42, which may be annular. In some embodiments, the retainer ring 36 may be disposed within the undercut 42. In some embodiments, a width 44 of the retainer ring 36 may be approximately equal to a length 46 of the undercut 42 such that a distal edge 48 of the retainer ring 36 and a proximal edge 50 of the retainer ring 36 may abut edges of the undercut 42. In some embodiments, the distal edge 48 and the proximal edge 50 may be annular. In some embodiments, the retainer ring 36 may fit snugly within the undercut 42. In some embodiments, an outer diameter may be slightly larger than a diameter of the undercut 42 such that the retainer ring 36 snaps into the undercut 42.

In some embodiments, the retainer ring 36 may be plastic, metal, or another suitable material. In some embodiments, the retainer ring 36 may be rigid or semi-rigid. In some embodiments, a durometer of the retainer ring 36 may be greater than a durometer of the annular valve 12. In some embodiments, the retainer ring 36 may be formed by molding. In further detail, in some embodiments, the retainer ring 36 may be formed by shaping a liquid or malleable raw material by using a fixed frame, such as a mold or a matrix. In some embodiments, the mold may include a hollow cavity receptacle, wherein the liquid or malleable raw material may be poured. In some embodiments, the liquid or malleable raw material may include plastic, metal, or another suitable material. As the liquid or malleable raw material hardens inside the mold, forming the retainer ring 36.

In some embodiments, the catheter system 18 may include a needle assembly 52. In some embodiments, the needle assembly 52 may include a needle hub 54 and an introducer needle 56 extending distally from the needle hub 54 and through the retainer ring 36, the annular valve 34, and the catheter 38. In some embodiments, the introducer needle 56 may include a sharp distal tip, which may facilitate placement of the catheter 38 within vasculature of a patient.

In some embodiments, the side port 32 may extend from a top of the catheter adapter 22 or a portion of the catheter adapter 22 opposite skin of the patient, which may be placed below the catheter adapter 22 and/or beneath one or more wings 58 extending outwardly from the catheter adapter 22.

Figure 2D:
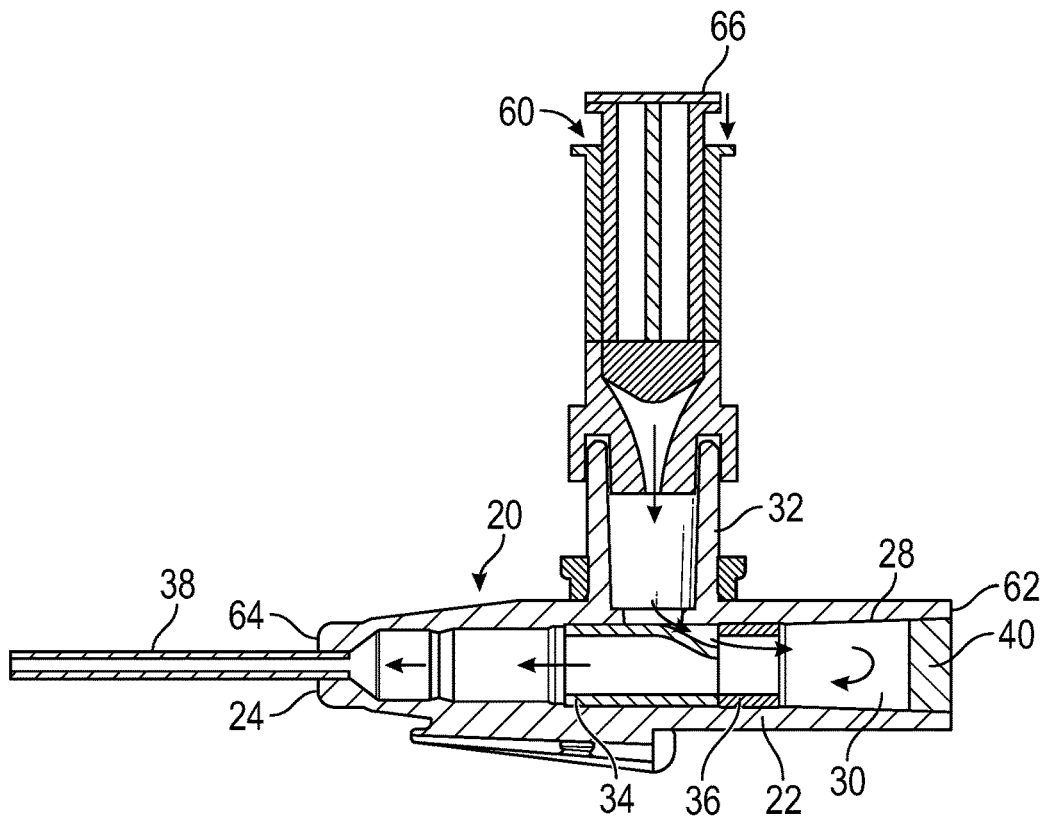
FIG. 2D is a cross-sectional view of the catheter system of FIG. 2A, illustrating an example infusion device coupled to an example side port and activated, according to some embodiments.

Referring now to FIG. 2D, in some embodiments, the side port 32 may be configured to receive an infusion device 60, which may include a syringe or another suitable infusion device configured to infuse fluid from the side port 32 into the lumen 30. In some embodiments, the retainer ring 36 is configured keep the annular valve 34 in a same position in response to fluid infusion through the side port 32 that opens the annular valve 34. In further detail, in some embodiments, the retainer ring 36 may be configured to reduce proximal movement of the annular valve 34 in response to fluid infusion through the side port 32 that opens the annular valve 34. In some embodiments, in response to fluid infusion through the side port 32 that opens the annular valve 34, a proximal end 62 of the annular valve 34 may not move in a proximal direction and/or a distal direction but may stay in place. Thus, in some embodiments, the retainer ring 36 may prevent fluid, such as blood and/or another fluid, from leaking through the annular valve 34 and out the side port 32.

In some embodiments, the infusion device 60 may be activated in order to flush the catheter system 18 or inject a bolus. In some embodiments, a method of flushing the catheter assembly 20 may include coupling the infusion device 60 to the side port 32 of the catheter adapter 22 of the catheter assembly 20. In some embodiments, the side port 32 may include a luer, such as, for example, a female luer, which may be configured to couple to a corresponding luer of the infusion device 60.

In some embodiments, the method may include activating the infusion device 60. In some embodiments, in response to activating the infusion device 60, the annular valve 34 may be opened to allow fluid to flow from the side port 32 into the lumen 30. In some embodiments, in response to activating the infusion device 60, the proximal end 62 of the annular valve 34 opposite a distal end 64 of the annular valve 34 may be forced against the retainer ring 36 and the retainer ring 36 may remain in place. In these and other embodiments, the proximal end 62 of the annular valve 34 may not move in a proximal direction and/or a distal direction but may stay in place.

In some embodiments, the infusion device 60 may include the syringe, as illustrated, for example, in FIG. 2D. In some embodiments, activating the infusion device 60 may include depressing a plunger 66 of the syringe or otherwise causing fluid to be expelled from the infusion device into the catheter assembly 20. In some embodiments, the method may include uncoupling and removing the needle assembly 52 from the catheter adapter 22, as illustrated, for example, in FIG. 2D. In some embodiments, the infusion device 60 may be activated after the needle assembly 52 is uncoupled and removed from the catheter adapter 22.

Figure 2E:
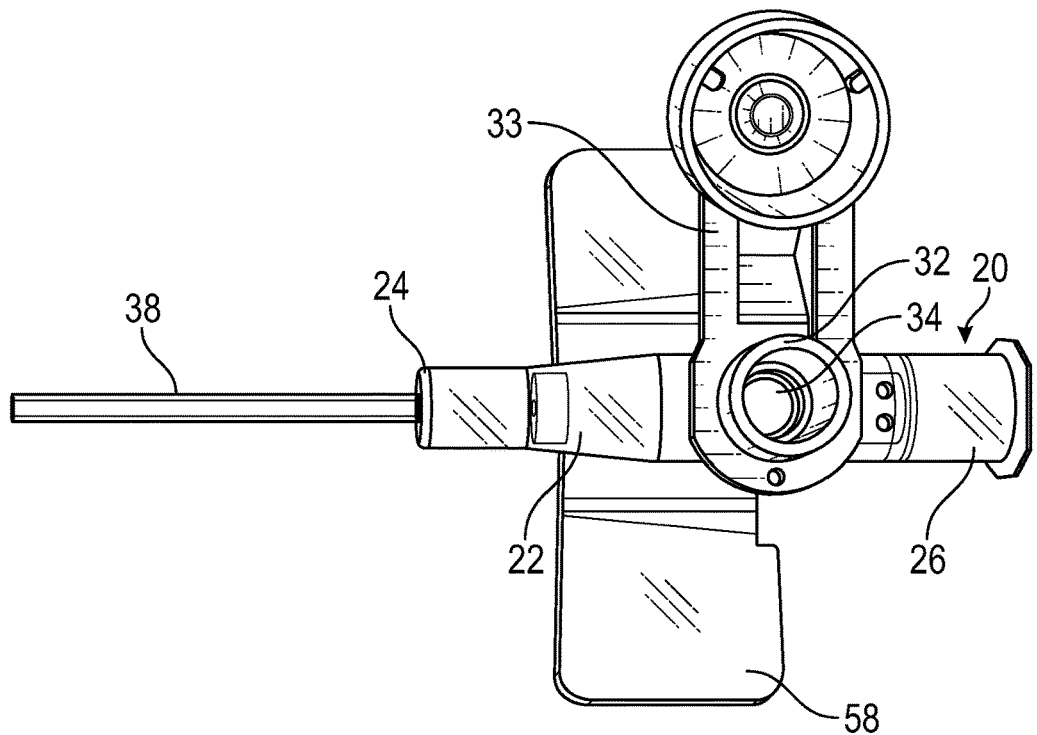
FIG. 2E is a top view of the catheter system following infusion through the side port, according to some embodiments.

Referring now to FIG. 2E, the catheter assembly 20 is illustrated with the cap 33 open after fluid infusion through the side port 32. As illustrated, the annular valve 34 is still in place and sealing the side port 32 after the fluid infusion.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:
  a catheter assembly, comprising:
    a catheter adapter, comprising a distal end, a proximal end, an inner surface forming a lumen, the lumen extending through the distal end and the proximal end, and a side port disposed between the distal end and the proximal end;
    an annular valve disposed within the lumen and aligned with the side port, wherein the annular valve seals a fluid pathway from the side port to the lumen;
    a retainer ring disposed proximal to and contacting the annular valve within the lumen; and
    a catheter extending distally from the distal end of the catheter adapter, wherein in response to fluid infusion through the side port, a proximal end of the annular valve is configured to open to allow fluid to flow proximally through the retainer ring.

2. The catheter system of claim 1, wherein the inner surface comprises an undercut, wherein the retainer ring is disposed within the undercut.

3. The catheter system of claim 1, wherein the annular valve comprises silicon.

4. The catheter system of claim 1, wherein the annular valve is cylindrical.

5. The catheter system of claim 1, wherein the retainer ring is formed by molding.

6. The catheter system of claim 1, wherein the retainer ring is plastic.

7. The catheter system of claim 1, further comprising a needle assembly, wherein the needle assembly comprises a needle hub and an introducer needle extending distally from the needle hub and through the retainer ring, the annular valve, and the catheter.

8. The catheter system of claim 1, wherein the side port extends from a top of the catheter adapter.

9. The catheter system of claim 1, wherein the side port is configured to receive a syringe.

10. The catheter system of claim 1, wherein the retainer ring is configured to reduce proximal movement of the annular valve in response to fluid infusion through the side port that opens the annular valve.

11. A method of flushing a catheter assembly, comprising:
  coupling an infusion device to a side port of a catheter adapter of the catheter assembly, wherein the catheter assembly comprises:
    a catheter adapter, comprising a distal end, a proximal end, an inner surface forming a lumen, the lumen extending through the distal end and the proximal end, and a side port disposed between the distal end and the proximal end;
    an annular valve disposed within the lumen and aligned with the side port, wherein the annular valve seals a fluid pathway from the side port to the lumen;
    a retainer ring disposed proximal and proximate the annular valve within the lumen; and
    a catheter extending distally from the distal end of the catheter adapter;
  activating the infusion device, wherein in response to activating the infusion device, a proximal end of the annular valve is opened to allow fluid to flow proximally through the retainer ring, wherein in response to activating the infusion device, a proximal end of the annular valve is forced against the retainer ring and the retainer ring remains in place.

12. The method of claim 11, wherein the infusion device comprises a syringe, wherein activating the infusion device comprises depressing a plunger of the syringe.

13. The method of claim 11, the inner surface comprises an undercut, wherein the retainer ring is disposed within the undercut.

14. The method of claim 11, wherein the annular valve comprises silicon.

15. The method of claim 11, wherein the annular valve is cylindrical.

16. The method of claim 11, wherein the retainer ring is formed by molding.

17. The method of claim 11, wherein the retainer ring is plastic.

18. The method of claim 11, further comprising uncoupling and removing a needle assembly from the catheter adapter, wherein the needle assembly comprises a needle hub and an introducer needle extending distally from the needle hub and through the retainer ring, the annular valve, and the catheter, wherein the infusion device is activated after the needle assembly is uncoupled and removed from the catheter adapter.

19. The method of claim 11, wherein the side port extends from a top of the catheter adapter.

20. The method of claim 11, wherein the catheter is a peripheral intravenous catheter.

* * * * *